(12) United States Patent
LeVaughn et al.

(10) Patent No.: US 10,143,777 B2
(45) Date of Patent: Dec. 4, 2018

(54) FENESTRATION KITS FOR MAKING FENESTRATED PLACENTAL TISSUE ALLOGRAFTS AND METHODS OF USING THE SAME

(71) Applicant: MiMedx Group, Inc., Marietta, GA (US)

(72) Inventors: Rick LeVaughn, Marietta, GA (US); Nicole Zabek, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

(21) Appl. No.: 14/942,989

(22) Filed: Nov. 16, 2015

(65) Prior Publication Data

US 2016/0136328 A1 May 19, 2016

Related U.S. Application Data

(60) Provisional application No. 62/080,898, filed on Nov. 17, 2014.

(51) Int. Cl.
| | |
|---|---|
| *A61K 35/50* | (2015.01) |
| *A61L 27/36* | (2006.01) |
| *A61L 27/58* | (2006.01) |
| *A61L 27/54* | (2006.01) |
| *A61L 15/40* | (2006.01) |
| *B26F 1/14* | (2006.01) |
| *B65B 7/02* | (2006.01) |
| *A61L 27/56* | (2006.01) |
| *A61L 27/60* | (2006.01) |

(52) U.S. Cl.
CPC ......... *A61L 27/3604* (2013.01); *A61L 15/40* (2013.01); *A61L 27/54* (2013.01); *A61L 27/56* (2013.01); *A61L 27/58* (2013.01); *A61L 27/60* (2013.01); *B26F 1/14* (2013.01); *B65B 7/02* (2013.01); *A61L 2300/412* (2013.01)

(58) Field of Classification Search
None
See application file for complete search history.

(56) References Cited

U.S. PATENT DOCUMENTS

| | | | | | |
|---|---|---|---|---|---|
| 1,938,318 | A | * | 12/1933 | Colby | B26F 1/24 423/392 |
| 4,964,992 | A | * | 10/1990 | Goldsmith | B01D 67/0025 210/500.36 |
| 8,323,701 | B2 | * | 12/2012 | Daniel | A61L 27/3604 424/582 |

(Continued)

FOREIGN PATENT DOCUMENTS

| | | | | | |
|---|---|---|---|---|---|
| WO | WO 12/112417 | * | 8/2012 | ............. | A61K 35/50 |
| WO | WO-2014/078080 A1 | | 5/2014 | | |

OTHER PUBLICATIONS

U.S. Appl. No. 13/815,747, Daniel et al, filed Mar. 15, 2013.*

(Continued)

*Primary Examiner* — Allison M Fox
(74) *Attorney, Agent, or Firm* — Alston & Bird LLP

(57) ABSTRACT

Described herein are fenestrated placental tissue allografts, methods for using the same for treating wounds that produce an exudate and to promote the healing process, and apparatus and kits for making the same that minimize or eliminate cross-contamination with placental tissue from other placental donors.

14 Claims, 6 Drawing Sheets

(56) References Cited

U.S. PATENT DOCUMENTS

| | | | |
|---|---|---|---|
| 8,372,437 B2 | 2/2013 | Daniel | |
| 8,409,626 B2* | 4/2013 | Daniel | A61L 27/3604 424/583 |
| 8,642,092 B2* | 2/2014 | Daniel | A61L 27/3604 424/583 |
| 8,703,207 B2* | 4/2014 | Daniel | A61L 27/3604 424/583 |
| 8,709,493 B2* | 4/2014 | Daniel | A61L 27/3604 424/583 |
| 8,709,494 B2* | 4/2014 | Daniel | A61L 27/3604 424/583 |
| 8,932,643 B2* | 1/2015 | Daniel | A61L 27/3604 424/583 |
| 9,084,767 B2* | 7/2015 | Daniel | A61L 27/3604 |
| 9,415,074 B2* | 8/2016 | Daniel | A61L 27/3604 |
| 2005/0105989 A1* | 5/2005 | Crudo | B26D 7/20 412/38 |
| 2010/0104539 A1 | 4/2010 | Daniel et al. | |
| 2011/0262515 A1 | 10/2011 | Lauritzen et al. | |
| 2013/0085570 A1* | 4/2013 | Rose | A61F 2/105 623/15.12 |
| 2013/0138222 A1 | 5/2013 | Horton et al. | |
| 2013/0202676 A1 | 8/2013 | Koob et al. | |
| 2014/0051059 A1 | 2/2014 | Pringle et al. | |
| 2014/0067058 A1 | 3/2014 | Koob et al. | |
| 2014/0205646 A1 | 7/2014 | Morse et al. | |

OTHER PUBLICATIONS

Yang, L., et al., "Living skin equivalents constructed using human amnions as a matrix," Journal of Dermatological Science, vol. 56, No. 3, pp. 188-195 (Dec. 2009).

International Search Report and Written Opinion for International Application No. PCT/US2015/060950 dated Feb. 3, 2016.

* cited by examiner

FENESTRATION KITS FOR MAKING FENESTRATED PLACENTAL TISSUE ALLOGRAFTS AND METHODS OF USING THE SAME

CROSS-REFERENCE TO RELATED APPLICATION

This application claims the benefit of U.S. Provisional Application No. 62/080,898, filed Nov. 17, 2014, which is incorporated herein by reference in its entirety.

FIELD OF THE INVENTION

This invention relates to fenestrated placental tissue allografts, methods for using the same for treating wounds that produce an exudate and to promote the healing process, and apparatus and kits for making the same that minimize or eliminate cross-contamination with placental tissue from other placental donors.

BACKGROUND

Human placental membrane (e g amniotic membrane) has been used for various types of reconstructive surgical procedures since the early 1900s. The membrane serves as a substrate material, more commonly referred to as a biological dressing or tissue graft. Such a membrane has also been used for ophthalmic procedures and more recently for dental regenerative procedures, treating ulcers, and as an adhesion barrier. Typically, the membrane is either frozen or dried for preservation and storage.

Placental tissue is typically harvested after an elective Cesarean surgery. The placenta is composed of the amniotic sac and sometimes is meant to include the umbilical cord and amniotic sac. The amniotic sac contains the amniotic fluid and protects the fetal environment.

The amniotic sac, commonly referred to as the amniotic membrane, has two primary layers of tissue, amnion and chorion. Amnion is the innermost layer of the amniotic sac and is in direct contact with the amniotic fluid. Histological evaluation indicates that the membrane layers of the amnion consist of a single layer of epithelium cells, thin reticular fibers (basement membrane), a thick compact layer, and a fibroblast layer. The fibrous layer of amnion (i.e., the basement membrane) contains collagen types IV, V, and VII, and cell-adhesion bio-active factors including fibronectin and laminins.

Placental tissue, such as amnion membrane, provides unique characteristics when used for surgical and wound-healing procedures, including providing a matrix for cellular migration/proliferation, providing a natural biological barrier, is non-immunogenic, and contains numerous bio-active molecules. Placental tissue can be used as a membrane to assist in tissue regeneration and improved healing outcomes in numerous applications. The amnion has the capability to self-adhere or, in the alternative, is susceptible of being fixed in place using different techniques, including fibrin glue or suturing.

Difficult-to-heal wounds are a common problem in hospital and clinical situations. Chronic wounds include, for example, venous stasis ulcers, decubitus ulcers and diabetic ulcers, and the like. Acute wounds include, for example, burns, skin graft donor sites, skin graft recipient sites, abrasions, and the like. In either case, the initial injury initiates inflammation, an early stage of the healing process. Mediators involved in inflammation, such as histamine, increase capillary permeability so that white blood cells can escape and the blood vessels leak more fluid. The excess fluid enters the wound where it forms the basis of what is referred to as an exudate. Exudate is derived from fluid that has leaked out of blood vessels and closely resembles blood plasma. Fluid leaks from capillaries into body tissues at a rate that is determined by the leakiness (permeability) of the capillaries and the pressures (hydrostatic and osmotic) across the capillary walls.

Exudate supports healing and a moist wound environment. The main role of exudate is to facilitate the diffusion of vital healing factors (e.g., growth and immune factors) and the migration of cells across the wound bed. It also promotes cell proliferation, provides nutrients for cell metabolism, and aids autolysis of necrotic or damaged tissue. In a wound that is not healing as expected, however, exudate production may continue and be excessive due to ongoing inflammatory or other processes. Although a moist environment is necessary for optimal wound healing, conditions of extreme wetness or dryness may adversely affect healing.

In the field of wound care, there exist several general categories of commonly used dressings, some of which aggressively adhere to a wound surface. For example, conventional gauze integrates into the wound as healing occurs and eschar forms on the wound surface. Other types of dressings are designed to adhere to the surrounding intact tissue around the wound site but not directly to the wound. However, such dressings often become dislodged or otherwise require frequent replacement during the healing process. As the dressings become dislodged or are replaced during dressing changes, the fragile epithelium can easily be damaged. Moreover, in the case of acute and chronic wounds, large amounts of exudate are typically produced which makes the use of such conventional dressings inferior as they generally do not properly manage wound exudate.

Placental tissue grafts have also been used for such purposes. These grafts, sometimes referred to as fenestration grafts, have holes manually punched through portions thereof to allow exudate to flow from the wound while the remaining portion of the graft releases growth factors and other cytokines to facilitate healing. However, these manually generated fenestration grafts lack reproducibility, are subject to tears and rips along the holes which adversely impact the graft's integrity, and extra care must be taken to prevent contamination of one fenestration graft with material from another fenestration graft.

Accordingly, there is a need to provide a biocompatible wound dressing that minimizes wound damage during the healing process and that is capable of managing exudate to ensure wound healing. There is a further need to produce a wound graft in a manner that allows commercial production that avoids tearing and cross-contamination during the production process in a cost- and time-efficient manner.

SUMMARY OF THE INVENTION

The present invention is predicated, at least in part, on the discovery that use of a fenestration kit as described herein reduces tearing and ripping of placental tissue allografts, while increasing reproducibility and safety (e.g., avoidance of cross-contamination by non-autologous placental tissue) of the allografts. The resulting fenestrated allografts are especially suited for wound healing applications, as the fenestrations allow for exudate to travel through the graft, while simultaneously providing sufficient surface area of the graft in contact with the wound to promote healing.

In view of the above, the processing of placental tissue requires that steps be taken to prevent cross-contamination from one processed placental tissue to the next. Such steps involve the assembly of sterile supplies and equipment in a staging area that is in a controlled, aseptic environment, and the placental tissue is prepared for introduction into the aseptic controlled environment as described herein. If the controlled environment is a manufacturing hood, the sterile supplies are opened and placed into the hood using conventional aseptic technique. If the controlled environment is a clean room or similarly aseptic room, the sterile supplies are opened and placed on a cart covered by a sterile drape. All work surfaces are covered by a piece of sterile drape using conventional aseptic techniques, and the sterile supplies and the processing equipment are placed on to the sterile drape, again using conventional aseptic techniques.

In addition, any processing equipment that is utilized with a first placental tissue must be decontaminated according to conventional and industry-approved decontamination procedures prior to the use of the equipment for processing a subsequent non-autologous placental tissue (i.e., from a different donor), which requires removing, decontaminating, and then re-introducing the equipment into the controlled environment. The continual decontamination of the processing equipment is time consuming, costly and inefficient, particularly in situations where it is desirable to process such tissue in commercial quantities.

According to one aspect of the present invention, there is described a fenestration kit and the use thereof to make a fenestrated placental tissue allograft as described herein, in a manner that allows for commercial production of tissue grafts using tissue from multiple placental donors, while avoiding cross-contamination of placental tissue with non-autologous tissue during the production process, in a cost- and time-efficient manner. In one embodiment, the fenestration kit is reusable. In a preferred embodiment, the fenestration kit is disposable.

According to one aspect of the invention, there is provided a fenestration kit for making a fenestrated placental tissue allograft, said kit comprising:

a cutting die comprising a substantially flat die surface having predetermined dimensions and having a first side and a second side, said first side having a plurality of prearranged cutting punches thereon, wherein the cutting die is made of a first material;

a cutting bed having substantially the same dimensions as the cutting die, wherein the cutting bed is made of a second material;

wherein the first material is harder than the second material.

In one embodiment, the first and/or second material is disposable. In one embodiment, the first and/or second material is reusable. In one embodiment, the first material is disposable and the second material is reusable. In one embodiment, the second material is disposable and the first material is reusable. In one embodiment, the first material is at least 10% harder than the second material based on an appropriate test as recognized in the art. In a preferred embodiment, the first material is at least 20% harder than the second material. In one embodiment, the test is ASTM test D2240.

In one embodiment, the fenestration kit further comprises a bag, said bag comprising a sealable opening and having at least the dimensions of said cutting die and said cutting bed. In a preferred embodiment, the bag is made of a material that will not puncture or break when the bag containing the cutting assembly is subjected to stress, e.g., run through a roller press.

In one embodiment, the cutting die, cutting bed, and the bag are sterilizable. In a preferred embodiment, the cutting die, cutting bed, and at least the interior of the bag are sterile.

The cutting punches should be spaced such that, when used to fenestrate an allograft, the resulting fenestrations/holes provide sufficient opportunity for the exudate produced by a wound to pass through the graft, while also maintaining sufficient allograft surface area to effectively treat the wound. In one embodiment, the cutting punches are spaced from about 5 mm to about 20 mm apart as measured from the center of two adjacent cutting punches. In one embodiment, the cutting punches are spaced from about 1.5 mm to about 10 mm apart as measured from the closest edge of one punch to the closest edge of an adjacent punch. In a preferred embodiment, the hole size (e.g., diameter) is about 20% to about 75% of the spacing distance. In a preferred embodiment, the cutting punches are substantially circular. In one embodiment, the cutting punches are at least about 0.5 mm in diameter. In a preferred embodiment, the cutting punches are between about 0.5 mm and about 5 mm in diameter.

It is contemplated that reproducible fenestration of allografts produced by the fenestration kit of the present invention will provide additional benefits. For example, when additional allografts are applied to a wound, the allograft can be applied such that the fenestrations of the additional/second allograft do not line up with the fenestrations from the original allograft. This allows the entirety of the wound to be covered by the allograft, albeit at different times. In one embodiment, the cutting punches are symmetrically distributed on the first side of the cutting die. In one embodiment, the cutting punches are uniformly distributed on the first side of the cutting die. In one embodiment, at least a portion of the cutting die does not contain cutting punches, for example around the edges of the die.

In one aspect of this invention is provided a method for making a fenestrated placental tissue allograft, said method comprising:
  i. providing a fenestration kit as described herein;
  ii. placing a placental tissue allograft on the cutting bed;
  iii. placing the cutting die on top of the allograft such that the first side of the cutting die is adjacent to said allograft, thereby creating an assembled fenestration kit; and
  vi. applying pressure to the assembled fenestration kit such that the cutting punches perforate the allograft, thereby fenestrating the allograft.

In a preferred embodiment, the assembled fenestration kit is placed into a bag and the bag is sealed prior to applying pressure to the fenestration kit.

In one embodiment, the placental tissue allograft is dehydrated prior to placing the allograft on the cutting bed. In one embodiment, the allograft is dehydrated after placing the allograft on the cutting bed. In one embodiment, the pressure is applied manually. In one embodiment, the pressure is applied mechanically. In a preferred embodiment, the pressure is applied by a roller press or like machine.

According to one aspect of this invention, there is described a fenestrated placental tissue allograft comprising a plurality of fenestrations such that when the fenestrated placental tissue allograft is applied to a wound, the fenestrations permit the necessary flow of exudate from the wound and through the graft to facilitate the healing process, while retaining sufficient coverage of the wound by the tissue allograft to assist in healing of the wound.

In some aspects, there is provided a fenestrated placental tissue allograft for treating a topical wound that produces an exudate. The allograft comprises placental tissue from a single placental donor and is made according to the methods described herein, such that it is substantially free of non-autologous placental tissue (i.e., tissue from another placental tissue donor). In a preferred embodiment, the allograft is completely free of non-autologous placental tissue.

In some aspects, the allograft comprises a first surface, a second surface and a plurality of prearranged passageways (fenestrations or holes) through the allograft. The passageways are distributed throughout the allograft in a prearranged pattern such that the remainder of the allograft contains a sufficient surface area substantially in direct contact with a wound when applied thereto so as to facilitate healing. Moreover, in a preferred embodiment, the number of passageways having ripping and tearing when prepared by the methods described herein are less than about 2 percent of the total passageways in the graft. This compares favorably with the number occurring from manually prepared allografts (greater than 5%).

In some aspects, the passageways are spaced from about 5 mm to about 20 mm apart, as measured from the center of two adjacent passageways. In some aspects, the passageways are spaced from 1.5 mm to 10 mm apart, as measured from the edge of one hole to the closest edge of an adjacent hole. In a preferred embodiment, the hole size (e.g., diameter) is about 20% to about 75% of the spacing distance. In some aspects, the passageways are substantially circular. In one embodiment, the circular passageways are at least 0.5 mm in diameter. In a preferred embodiment, the passageways are between about 0.5 mm and about 5 mm in size (e.g., diameter).

According to the methods of the present invention, the passageways are substantially free of allograft tissue obstruction so as to permit the free flow of exudate away from the wound and through the passageways. Accordingly, the allograft according to the present invention facilitates healing of wounds without substantial contamination from non-autologous placental tissue.

In some aspects, the allografts according to the present invention are useful for treating acute wounds. Acute wounds include, but are not limited to, burns, skin graft donor sites, skin graft recipient sites, abrasions, and the like.

In some aspects, the allografts according to the present invention are useful for treating chronic wounds. Chronic wounds include, but are not limited to, venous stasis ulcers, decubitus ulcers, diabetic ulcers, and the like.

In some aspects, a wound dressing comprising the allograft of the present invention is provided.

In some aspects, the allograft is dehydrated. In one embodiment, the allograft is dehydrated prior to fenestration. In one embodiment, the allograft is dehydrated after fenestration.

Exemplary placental tissue grafts that can be utilized in accordance with the present invention have been described previously, such as in U.S. Pat. Nos. 8,323,701; 8,372,437; and U.S. Patent Publication Nos. 2014/0052247; 2014/0067058; 2014/0205646; and 2013/0202676; each of which is incorporated by reference herein in its entirety. For example, these grafts can include one or several layers of amnion tissue, combined with chorion and/or other biocompatible membranes to form tissue grafts.

In one embodiment, the allograft comprises at least one layer of amnion tissue where the epithelium layer has been substantially removed in order to expose the basement layer to host cells. By removing the epithelium layer, it is believed that cells from the host can more readily interact with the cell-adhesion bio-active molecules located onto top and throughout the basement membrane of the amnion. In one embodiment, the epithelium layer is not removed from at least one amnion layer of the allograft. In a preferred embodiment, the fibroblast cellular layer on at least one amnion layer of the allograft is substantially intact.

In some aspects, the fenestrated allograft comprises one or several layers of amnion, and optionally further comprises at least one layer of chorion or other biocompatible membrane. In one embodiment, the epithelium layer of at least one amnion layer has been substantially removed in order to expose the basement layer.

In some aspects, there is provided a method for treating a topical wound that produces an exudate. The method comprises placing on a wound a fenestrated placental tissue allograft according to the present invention and maintaining the allograft on the wound. In one embodiment, the method further comprises removing the exudate using negative pressure protocols known in the art and as described herein.

In one embodiment, the method further comprises placing additional allografts according to the present invention onto the wound. Additional allografts may be required, for example, when the allograft is absorbed or partially absorbed by the wound. In another embodiment, the first allograft is removed and a second allograft is applied to the wound. In a preferred embodiment, the additional or second allograft is placed adjacent to the wound such that all or most of the fenestrations present on the second allograft are adjacent to areas of the wound that had previously been covered by the allograft.

In some aspects, there is provided a method for making the fenestrated placental tissue allograft according to the present invention, wherein a sterile cutting die and a sterile cutting bed are provided. The cutting die comprises a substantially flat die surface having predetermined dimensions and a plurality of prearranged cutting punches distributed on the flat die surface. In one embodiment, the cutting punches are uniformly spaced. In one embodiment, the cutting punches are symmetrically spaced. The sterile cutting bed comprises substantially the same dimensions as the cutting die and is suitable for placement of a desired placental tissue thereon.

According to the method of the present invention, the placental tissue, which comprises a first surface and a second surface, is placed between the cutting die and the cutting bed to form a cutting assembly. The cutting assembly is then placed into a sealable cutting bag, such as a plastic bag, Tyvek bag, and the like. Uniform pressure is then applied to the cutting assembly such that the cutting punches pierce the placental tissue to form a plurality of prearranged passageways in direct communication with the first surface and the second surface of the placental tissue. In one embodiment, the passageways are uniformly distributed throughout the allograft. In one embodiment, the passageways are substantially free of allograft tissue obstruction. As would be understood by one skilled in the art, the uniform pressure can be applied manually or with a machine, e.g. a roller press or like apparatus.

In some aspects, the passageways are spaced from about 1.5 mm to about 20 mm apart as measured from the center of two adjacent passageways. In some aspects, the passageways are substantially circular. In one embodiment, the circular passageways are at least 0.5 mm in diameter.

In some aspects, there is provided a manufacturing kit for making a fenestrated placental tissue allograft according to the present invention. The manufacturing kit according to the present invention comprises a sterile cutting die, a sterile cutting bed, and a sterile cutting bag as described herein.

According to the present invention, the fenestrated placental tissue allograft is highly suited for use in a broad range of applications including the treatment of acute wounds, chronic wounds, and other wounds where an exudate (or transudate) is produced.

The advantages of the invention will be set forth in part in the description which follows, and in part will be apparent from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
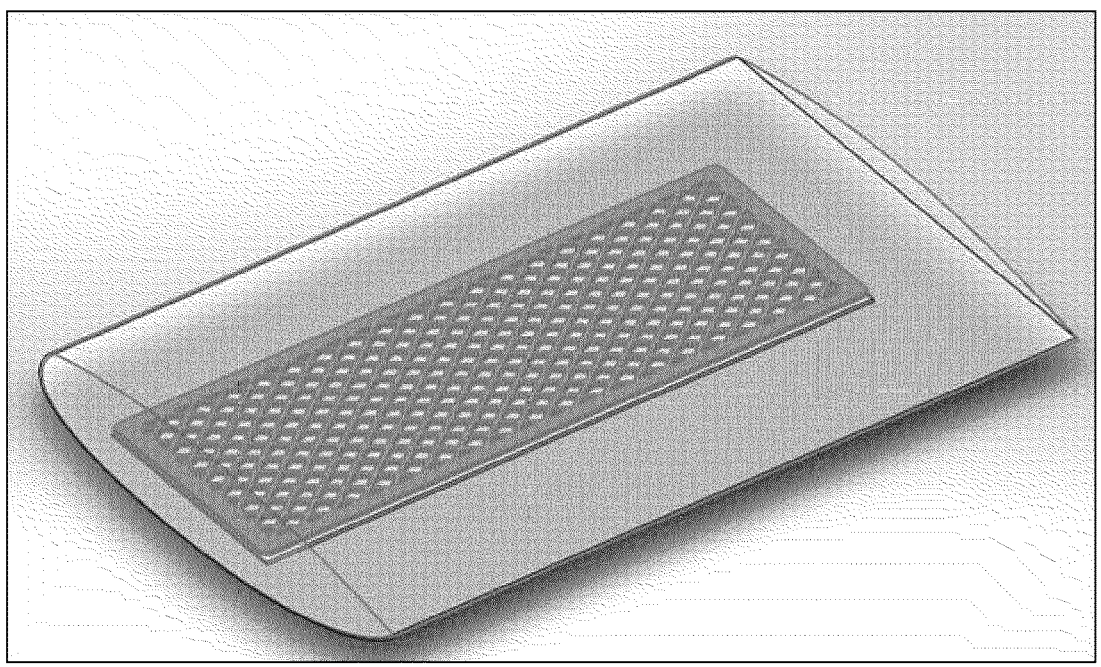
FIG. 1 depicts an exemplary fenestration kit according to the present invention.

Before the present invention is disclosed and described, it is to be understood that the aspects described below are not limited to specific compositions, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a cross-linking agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" as used herein is any vertebrate organism including mammals such as domesticated animals and primates such humans. In a preferred embodiment, the subject is a human.

The term "about" as used herein indicates that a value can vary by up to ±5%, for example ±5%, ±2%, or ±1%.

The terms "hard" and "hardness" are used interchangeably herein to refer to the resistance of a material to permanent shape change when a compressive force is applied. A material that is harder than another is more resistant to permanent shape change. In a preferred embodiment, the hardness of a material is determined based on shore hardness. Shore hardness is a measure of the resistance of the material (e.g., plastic or polymer) to indentation. The higher the number, the greater the resistance (hardness). In an especially preferred embodiment, the ASTM test D2240 is used. However, one of skill in the art would recognize that any appropriate test can be used to determine the relative hardness of the two materials, and the appropriate test is dependent upon, inter alia, the type of material to be tested.

The term "amnion" as used herein includes amniotic membrane where the intermediate tissue layer is intact or has been substantially removed. The amnion preferably is obtained from the placenta. In some embodiments, the amnion is obtained from the umbilical cord.

The term "placental tissue" refers to any and all of the well-known components of the placenta including but not limited to amnion, chorion, and when referring to umbilical cord as part of the placenta—Wharton's Jelly, and the like. In one preferred embodiment, the placental tissue does not include any of the umbilical cord components (e.g., Wharton's jelly, umbilical cord vein and artery, and surrounding membrane). In a preferred embodiment, the placental tissue is modified typically by removing the intermediate layer between the amnion and chorion such that the resulting tissue graft lacks this layer.

The term "placental tissue graft" refers to any combination of placental tissue which contains either an amnion or a chorion layer and optionally additional layers which may or may not be obtained from the placenta. Preferably, the placental tissue graft lacks an intermediate layer. Single layers of amnion or chorion can be used. However, preferably multiple layers of amnion and/or chorion form the tissue graft, which layers are typically dehydrated and laminated together. The amnion can optionally be partially or completely decellularized such as by removing substantially all of the epithelial layer and/or the fibroblast layer. Examples of placental tissue grafts suitable for this invention include by way of example U.S. Pat. Nos. 8,323,701; 8,372,437; and U.S. Patent Publication Nos. 2014/0052247; 2014/0067058; 2014/0205646; and 2013/0202676.

The terms "fenestration" and "fenestrated" may be used interchangeably and refer to placental tissue grafts which have been further modified to include a plurality of prearranged holes (fenestrations) in the tissue graft. Such holes allow exudate to traverse through the tissue graft. Further, the number and size of the holes is predetermined so as to ensure that the remaining placental tissue covers a sufficient surface area of the wound to be effective in treating the wound.

As used herein, the term "non-autologous tissue" refers to placental tissue from a different placenta donor.

As used herein, the term "exudate" also includes transudate. Transudate is similar to exudate, but contains less protein.

Titles or subtitles may be used in the specification for the convenience of a reader, which are not intended to influence the scope of the present invention. Additionally, some terms used in this specification are more specifically defined below.

Tissue Grafts and Methods for Making Thereof

Described herein are fenestrated placental tissue allografts and methods for their use. Preferred placental tissue allografts used in preparing the fenestrated derivatives thereof can be prepared by the exemplary route described below.

A brief overview of certain aspects of the steps to harvest, process, and prepare placental material for later use as a tissue graft are described. More detailed descriptions and discussion regarding each individual step will follow. Initially, the placenta tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the amnion and chorion then takes place (step 130). Acceptable tissue is then decontaminated (step 140), followed by the optional steps of substantially removing the epithelium layer from the placental tissue to expose the basement membrane (step 145) and optionally cross-linking of the placental tissue(s) (step 147) used to prepare the tissue grafts. The tissue graft is then prepared from the placental tissue and the graft is subsequently dehydrated (step 150), cut and packaged (step 160), sterilized using gamma radiation or electron beam radiation, and released (step 170) to the market for use by medical professionals for wound care. Fenestration may be added at any step. Preferably, fenestration occurs after dehydration and prior to packaging. Each step is described in detail below.

Initial Tissue Collection (Step 110)

The components used to produce the tissue grafts are derived from the placenta. The source of the placenta can vary. In one aspect, the placenta is derived from a mammal such as human and other animals including, but not limited to, cows, pigs, and the like can be used herein. In the case of humans, the recovery of the placenta originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion of obtaining the results from the screening tests and delivery cultures, such tissue is labeled and kept in quarantine. The placenta is approved for further processing only after the required screening assessments and delivery cultures, which declare the tissue safe for handling and use, are satisfied and obtains final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue are assembled in a staging area in a controlled (i.e., aseptic) environment and are prepared for introduction into the controlled environment. In one aspect, the placenta is processed at room temperature. If the controlled environment is a manufacturing hood, the sterile supplies are opened and placed into the hood using conventional aseptic techniques. If the controlled environment is a clean room, the sterile supplies are opened and placed on a cart covered by a sterile drape. All the work surfaces are covered by a piece of sterile drape using conventional aseptic technique, and the sterile supplies and the processing equipment are placed onto the sterile drape, again using conventional aseptic technique.

Processing equipment is decontaminated according to conventional and industry-approved decontamination procedures and then introduced into the controlled environment. The equipment is strategically placed within the controlled environment to minimize the chance for the equipment to come in proximity to or be inadvertently contaminated by the tissue specimen.

Next, the placenta is removed from the sterile shipment bag and transferred aseptically to a sterile processing basin within the controlled environment. The sterile basin contains hypertonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

The amnion and chorion are next carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion can be separated from the chorion. The amnion appears as a thin, opaque layer on the chorion.

The fibroblast layer is identified by gently contacting each side of the amnion with a piece of sterile gauze or a cotton tipped applicator. The fibroblast layer will stick to the test material. The amnion is placed into processing tray basement membrane layer down. Using a blunt instrument, a cell scraper, or sterile gauze, any residual blood is also removed. This step must be done with adequate care, again, so as not to tear the amnion. The cleaning of the amnion is complete once the amnion is smooth and opaque-white in appearance.

The methods described herein do not remove all cellular components in the amnion. This technique is referred to in the art as "decellularization." Decellularization generally involves the physical and/or chemical removal of all cells present in the amnion, which includes epithelial cells and fibroblast cells. For example, although the removal of epithelial cells is optional, the fibroblast layer present in the amnion stromal layer is intact, even if the intermediate tissue layer is removed. Here, fibroblast cells are present in the fibroblast layer. Optionally, the epithelial cells are present as well, as described below.

In certain aspects, the intermediate tissue layer, also referred to as the spongy layer, is substantially removed from the amnion in order to expose the fibroblast layer. The term "substantially removed" with respect to the amount of intermediate tissue layer removed is defined herein as removing greater than 90%, greater than 95%, or greater than 99% of the intermediate tissue layer from the amnion. This can be performed by peeling the intermediate tissue layer from the amnion. Alternatively, the intermediate tissue layer can be removed from the amnion by wiping the intermediate tissue layer with gauze or other suitable wipe. The resulting amnion can be subsequently decontaminated using the process described below. Not wishing to be bound by theory, the removal of the intermediate layer can accelerate the drying of the tissue graft, particularly if multiple amnion membranes are used to produce the graft.

Chemical Decontamination (Step 140)

The amnion and chorion isolated above can be chemically decontaminated using the techniques described below. In one aspect, the amnion and chorion is decontaminated at room temperature. In one aspect, the amnion produced in step 130 can be placed into a sterile Nalgene jar for the next step. In one aspect, the following procedure can be used to clean the amnion. A Nalgene jar is aseptically filled with 18% saline hypertonic solution and sealed (or sealed with a top). The jar is then placed on a rocker platform and agitated for between 30 and 90 minutes, which further cleans the amnion of contaminants If the rocker platform was not in the critical environment (e.g., the manufacturing hood), the Nalgene jar is returned to the controlled/aseptic environment and opened. Using sterile forceps or by aseptically decanting the contents, the amnion is gently removed from the Nalgene jar containing the 18% hypertonic saline solution and placed into an empty Nalgene jar. This empty Nalgene jar with the amnion is then aseptically filled with a premixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion. This jar or container containing the amnion and antibiotics is then sealed or closed and placed on a rocker platform and agitated for, preferably, between 60 and 90 minutes. Such rocking or agitation of the amnion within the antibiotic solution further cleans the tissue of contaminants and bacteria. Optionally, the amnion can be washed with a detergent. In one aspect, the amnion can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion and antibiotics is then returned to the critical/aseptic environment and opened. Using sterile forceps, the amnion is gently removed from the jar or container and placed in a sterile basin containing sterile water or normal saline (0.9% saline solution). The amnion is allowed to soak in place in the sterile water/normal saline solution for at least 10 to 15 minutes. The amnion may be slightly agitated to facilitate removal of the antibiotic solution and any other contaminants from the tissue. After at least 10 to 15 minutes, the amnion is ready to be dehydrated and processed further.

In the case of chorion, the following exemplary procedure can be used. After separation of the chorion from the amnion and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the decontamination of amnion. The container is sealed and agitated without heat for 15 minutes to 120 minutes. The chorion tissue is next washed with deionized water (250 ml of DI water×4) with vigorous motion for each rinse. The tissue is removed and placed into a container of 1× PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

Optional Removal of Epithelium Layer from Placental Tissue (Step 145)

In certain aspects, it is desirable, although optional, to remove the epithelium layer present on the placental tissue. In one aspect, the epithelium layer present on the amnion is substantially removed in order to expose the basement layer of the amnion. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper. Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and the before the tissue has been dehydrated as described in the next section. For example, a representative sample graft is removed for microscopic analysis. The tissue sample is place onto a standard slide, stained with Eosin Y and viewed under the microscope. If epithelium is present, it will appear as cobblestone-shaped cells.

The methods described herein, particularly steps 130 and 145, do not remove all cellular components in the amnion. This technique is referred to in the art as "decellularization." Decellularization generally involves the physical and/or chemical removal of all cells present in the amnion, which includes epithelial cells and fibroblast cells. Although step 145 does remove epithelial cells, the fibroblast layer present in the amnion stromal layer is intact (i.e., includes fibroblast cells), even after removal of the intermediate layer discussed in step 130.

Optional Cross-Linking Step (Step 147)

Depending upon the application of the tissue graft, one or more placental tissues used to produce the tissue graft can be optionally cross-linked. Not wishing to be bound by theory, the cross-linking of the placental tissue can modify the resorption properties of the placental tissue. For example, the placental tissue can be cross-linked in order to regulate the rate of release of growth factors present in the placental tissue. In other aspects, the cross-linked placental tissue can be sufficiently cross-linked in order to prevent bioactive agents (e.g., INFUSE®) from leaching out of the tissue graft. Here, the cross-linked placental tissue acts as a barrier.

The placental tissue grafts can be cross-linked using a number of techniques. In one aspect, cross-linking may be achieved by chemical, thermal, radiation, fibronectin, fibrinogen and/or hydrogel cross-linking methods. In other aspects, the placental tissue can be individually treated with a cross-linking agent prior to lamination and formation of the tissue graft. In general, the cross-linking agent is non-toxic and non-immunogenic. When two or more placental tissues are treated with the cross-linking agent, the cross-linking agent can be the same or different. In one aspect, the chorion and amnion can be treated separately with a cross-linking agent or, in the alternative, the chorion and amnion can be treated together with the same cross-linking agent. In certain aspects, the amnion or chorion can be treated with two or more different cross-linking agents. Exemplary cross-linked placental tissue grafts and methods of cross-linking are described in U.S. Patent Application Publication Nos. 2014/0052247; 2014/0205646; 2013/0202676, each of which is incorporated herein in its entirety.

Optional Preparation of Reinforced Tissue Allografts

In one aspect, after the placental tissue has been prepared, a reinforced tissue allograft may be produced by laminating one or more placental tissues on each side of a biocompatible mesh.

In one aspect, the biocompatible mesh can be made from non-resorbable materials including but not limited to biocompatible metals such as titanium alloys, stainless steel, cobalt-chromium alloys, and nickel-titanium alloys. In another aspect, the layer of biocompatible mesh can be made from non-resorbable polymeric materials, including but not limited to, thermoplastic resins, polyethylenes, ultra-high weight molecular weight polyethylene, high molecular weight polyolefins, uncoated monofilament polypropylene, polyether ether ketone, polyethylene terephthalate, polytetrafluoroethylene, expanded polytetrafluoroethylene, nylon, any polymer or aliphatic hydrocarbons containing one or more double bonds, any other appropriate porous materials, or any other appropriate porous material that can be bent or otherwise formed into a shape.

In another aspect, the biocompatible mesh can be composed of a synthetic or biological resorbable polymeric material including but not limited to polyglycolic acid, poly-L-lactic acid (PLLA),poly-D,L-lactic acid (PDLA), trimethylenecarbonate (TMC), poly-ε-caprolactone, poly-P-dioxanone, copolymers of lactide and glycolide (PLGA), polyhydroxy-3-butyrate, collagen, hyaluronic acid, silk, biocellulose, other protein-based polymers, polysaccharides, poly(DTE carbonate), polyarylates, blends of PLLA, PLDA, or PLGA with TMC and other combinations of these polymers.

The reinforced tissue grafts are generally a sandwich structure composed of one or more placental tissues laminated on each side of the biocompatible mesh. Exemplary reinforced placental tissue allografts and methods of making can be found in U.S. Patent Application Publication No. 2014/0067058, which is incorporated herein by reference in its entirety.

In certain aspects, a bioactive agent can be added to the placental tissue prior to and/or after lamination and production of the allograft. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the allograft with bioactive agent to the region of interest, the bioactive agent is delivered to the region over time. Thus, the allografts described herein are useful as delivery devices of bioactive agents and other pharmaceutical agents when administered to a subject.

Lamination and Dehydration (Step 150)

The preparation of the placental tissue allografts generally involves the sequential layering of placental tissue or other biocompatible material (e.g., mesh, non-placental tissues and the like). In one aspect, one or more placental tissues (i.e., the first membrane) can be placed on the surface of a drying fixture or other surface. In one embodiment, one or more placental tissue is layered on the cutting bed. The first membrane is preferably amnion or chorion. In some embodiments, one or more additional membranes are layered on top of the first membrane. The one or more additional membranes may comprise a biocompatible mesh, amnion, chorion, allograft pericardium, allograft acellular dermis, amniotic membrane, Wharton's jelly, purified xenograft Type-1 collagen, biocellulose polymers or copolymers, biocompatible synthetic polymer or copolymer films, purified small intestinal submucosa, bladder acellular matrix, cadaveric fasia, or any combination thereof. In a preferred embodiment, the one or more additional membranes is not Wharton's jelly. Without being bound by theory, it is expected that addition of Wharton's jelly to the allograft would make fenestration more difficult.

In one embodiment, the placental tissue is layered on the cutting bed. In one embodiment, the placental tissue is fenestrated prior to dehydration.

In certain aspects, adhesives such as, for example fibrin glue and hydrogels, can be used to adhere the placental tissues together as well as to other layers of the allograft. Fibrin glue is prepared from pooled blood and has the potential to transmit disease. At this time, the application of fibrin glue to seal dural tears constitutes off-label use. Synthetic hydrogels such as the DuraSeal Spine Sealant System (Confluent Surgical Inc., Waltham, Mass.) consist of two components (polyethylene glycol ester and trilysine amine) and a delivery system which polymerize at the defect site to form a seal. As the hydrogel swells to up to 50% in size during polymerization, neural compression may occur.

Once the placental tissue allograft is produced, the allograft is dehydrated. In one aspect, a drying fixture with the allograft thereon is placed in a freeze-dryer. The use of the freeze-dryer to dehydrate the allografts can be more efficient and thorough compared to other techniques such as thermal dehydration. In general, it is desirable to avoid ice crystal formation in the placental tissue allograft as this may damage the extracellular matrix in the allograft. By chemically dehydrating the placental tissue prior to freeze-drying, this problem can be avoided.

In another aspect, the dehydration step involves applying heat to the allograft. In one aspect, the drying fixture with the allograft is placed in a sterile Tyvek (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvek bag or, alternatively, placed into a suitable mounting frame that is designed to hold multiple drying frames thereon and the entire frame is then placed into a larger, single sterile Tyvek dehydration bag and sealed.

The Tyvek dehydration bag containing the one or more drying fixtures is then placed into a non-vacuum oven or incubator that has been preheated to approximately 35 to 50 degrees Celsius. The Tyvek bag remains in the oven for between 30 to 120 minutes. In one aspect, the heating step can be performed at 45 minutes at a temperature of approximately 45 degrees Celsius to dry the tissue sufficiently but without over-drying or burning the allograft. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

In another aspect, the allograft is dehydrated by chemical dehydration followed by freeze-drying. In one aspect, the chemical dehydration step is performed by contacting the placental tissue independently or as a laminate with a polar organic solvent for a sufficient time and amount in order to substantially (i.e., greater than 90%, greater than 95%, or greater than 99%) or completely remove residual water present in the placental tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the tissue can be freeze-dried directly as discussed below.

After chemical dehydration, the allograft is freeze-dried in order to remove any residual water and polar organic solvent. In one aspect, the tissue graft can be laid on a suitable drying fixture prior to freeze-drying.

In another aspect, the placental tissue allografts described herein can be dehydrated using an innovative dehydration device which enhances the rate and uniformity of the dehydration process. Exemplary dehydration devices are described in U.S. Patent Application Publication No. 2014/0051059 and PCT Publication No. WO2014/078080, each of which is incorporated herein by reference in its entirety.

Fenestration

Fenestration of the placental tissue allograft may be performed before or after the dehydration step. In a preferred embodiment, the fenestration step is performed after the dehydration step. In one embodiment, the fenestration step is performed prior to cutting the placental tissue allograft. In one embodiment, the fenestration step is performed after cutting the placental tissue allograft.

Figure 2:
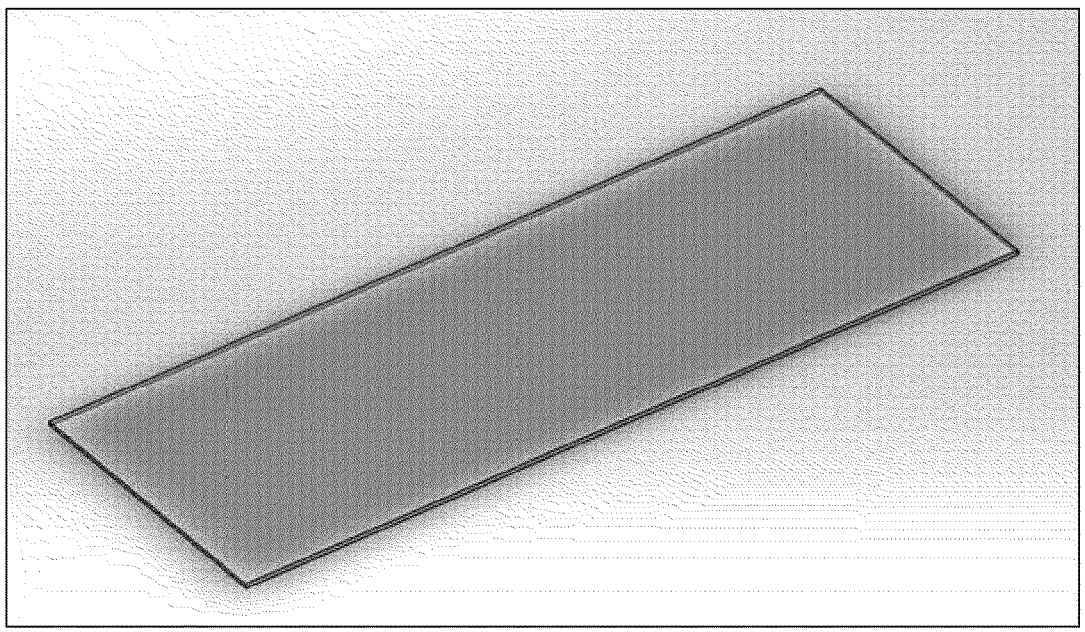
FIG. 2 depicts an exemplary cutting bed according to the present invention.

Fenestration is performed using a fenestration kit. An exemplary kit is shown in FIG. 1. In one embodiment, the fenestration kit comprises:

a cutting die comprising a die surface having predetermined dimensions and having a first side and a second side, said first side having a plurality of prearranged cutting punches thereon, wherein the cutting die is made of a first material;

a cutting bed (e.g., as shown in FIG. 2) having substantially the same dimensions as the cutting die, wherein the cutting bed is made of a second material.

In one embodiment, the first material and/or second material are disposable. In one embodiment, the first and/or second material is reusable. In one embodiment, the first and second material are biologically compatible. In a preferred embodiment, the first material is harder than the second material. In one embodiment, the hardness of each material is measured by a Shore test or a Rockwell test. In an especially preferred embodiment, the hardness of the materials is determined by ASTM test number ASTM D2240 (ISO test number ISO 868).

In one embodiment, the cutting die is substantially flat. As used herein, the term "substantially flat" refers to a cutting die that is flat except for the cutting punches and other protrusions from the surface of the die. In one embodiment, the cutting die is configured such that the cutting die and cutting bed fit together, such that the cutting die and the cutting bed do not come apart (or do not easily come apart) when assembled with the allograft. In a preferred embodiment, the cutting die and cutting bed fit together such that the assembled fenestration kit does not come apart when it is put into and/or transported with the bag. However, it is important that the cutting die and cutting bed come apart after fenestration of the allograft. If the assembled fenestration kit is too difficult to take apart after fenestration of the allograft, there is a risk of tearing or ripping the allograft during this step.

In one embodiment, the cutting die comprises a material that is at least about 10% harder than the material comprising the cutting bed, as measured by a Shore test. In a preferred embodiment, the cutting die comprises a material that is at least about 20% harder than the material comprising the cutting bed. In one embodiment, the cutting die comprises a material that is at least about 30% harder than the material comprising the cutting bed. In one embodiment, the cutting die comprises a material that is at least about 40% harder than the material comprising the cutting bed. In one embodiment, the cutting die comprises a material that is at least about 60% harder than the material comprising the cutting bed. In one embodiment, the cutting die comprises a material that is at least about 80% harder than the material comprising the cutting bed. In one embodiment, the cutting die comprises a material that is at least about 100% harder than the material comprising the cutting bed.

In one embodiment, the cutting die comprises a material that is about 10% to about 200% harder than the material comprising the cutting bed. In one embodiment, the cutting die comprises a material that is about 20% to about 200% harder than the material comprising the cutting bed. In one embodiment, the cutting die comprises a material that is about 30% to about 200% harder than the material comprising the cutting bed. In one embodiment, the cutting die comprises a material that is about 40% to about 200% harder than the material comprising the cutting bed. In one embodiment, the cutting die comprises a material that is about 60% to about 200% harder than the material comprising the cutting bed. In one embodiment, the cutting die comprises a material that is about 80% to about 200% harder than the material comprising the cutting bed. In one embodiment, the cutting die comprises a material that is about 100% to about 200% harder than the material comprising the cutting bed. In one embodiment, the cutting die comprises a material that is about 10% to about 100% harder than the material comprising the cutting bed. In one embodiment, the cutting die comprises a material that is about 20% to about 100% harder than the material comprising the cutting bed. In one embodiment, the cutting die comprises a material that is about 30% to about 100% harder than the material comprising the cutting bed. In one embodiment, the cutting die comprises a material that is about 40% to about 100% harder than the material comprising the cutting bed. In one embodiment, the cutting die comprises a material that is about 60% to about 100% harder than the material comprising the cutting bed. In one embodiment, the cutting die comprises a material that is about 80% to about 100% harder than the material comprising the cutting bed. Relative hardness includes ranges or values within any of these ranges (including endpoints).

Exemplary materials that can be used for the cutting die include, without limitation, polypropylene, styrene, high-impact polystyrene, polyvinylchloride, nylon, acrylic, high-density polyethylene, polycarbonate, and any other hard plastic. Metals, especially metals that do not rust and/or corrode easily, can also be used for the cutting die. In one embodiment, the cutting die comprises stainless steel. In a preferred embodiment, the cutting die comprises polypropylene.

Exemplary materials that can be used for the cutting bed include, without limitation, low-density polyethylene, polyethylene terephthalate, polycarbonate, polystyrene, silicone rubber, isoprene rubber, or any other plastic or rubber material. In a preferred embodiment, the cutting bed comprises low-density polyethylene. Metals, especially metals that do not rust and/or corrode easily, can also be used for the cutting bed. When a metal is used, the cutting bed preferably includes holes that are sized such that the cutting punches can fit within the holes when the cutting die and cutting bed are assembled. In one embodiment, the cutting bed comprises stainless steel. In one embodiment, the cutting die comprises stainless steel and the cutting bed comprises low-density polyethylene.

The dimensions of the cutting die and/or cutting bed may be any dimensions that will hold a placental tissue or portion thereof. In one embodiment, the dimensions are about 2 mm×2 mm to about 240 mm×240 mm. Preferred sizes include, without limitation, 9 mm×20 mm, 9 mm×15 mm, 9 mm×9 mm, 6 mm×16 mm, 6 mm×10 mm, & 4 mm×10 mm.

The cutting punches should be spaced such that, when used to fenestrate an allograft, the resulting fenestrations/holes provide sufficient opportunity for the exudate produced by a wound to pass through the graft, while also maintaining sufficient allograft surface area to effectively treat the wound.

In one embodiment, the cutting punches are spaced from about 5 mm to about 20 mm apart as measured from the center of two adjacent cutting punches. In one embodiment, the cutting punches are spaced from about 10 mm to about 20 mm apart as measured from the center of two adjacent cutting punches. In one embodiment, the cutting punches are spaced from about 5 mm to about 10 mm apart as measured from the center of two adjacent cutting punches. This includes ranges or values within any of these ranges (including endpoints). In one embodiment, the cutting punches are spaced about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm apart as measured from the center of two adjacent cutting punches.

In one embodiment, the cutting punches are spaced from about 1.5 mm to about 10 mm apart as measured from the outer edge of one punch to the closest outer edge of an adjacent punch. In one embodiment, the cutting punches are spaced from about 3 mm to about 10 mm apart as measured from the outer edge of one punch to the closest outer edge of an adjacent punch. In one embodiment, the cutting punches are spaced from about 5 mm to about 10 mm apart as measured from the outer edge of one punch to the closest outer edge of an adjacent punch. In one embodiment, the cutting punches are spaced from about 8 mm to about 10 mm apart as measured from the outer edge of one punch to the closest outer edge of an adjacent punch. This includes ranges or values within any of these ranges (including endpoints). In one embodiment, the cutting punches are spaced about 1.5 mm, about 2 mm, about 3 mm, about 4 mm, about 5 mm, about 6 mm, about 7 mm, about 8 mm, about 9 mm, or about 10 mm apart as measured from the outer edge of one punch to the closest outer edge of an adjacent punch.

In a preferred embodiment, the size of the cutting punch (e.g., diameter) is about 20% to about 75% of the spacing distance between cutting punches. In one embodiment, the size of the cutting punch (e.g., diameter) is about 20% to about 60% of the spacing distance. In one embodiment, the size of the cutting punch (e.g., diameter) is about 20% to about 50% of the spacing distance. In one embodiment, the size of the cutting punch (e.g., diameter) is about 20% to about 40% of the spacing distance. In one embodiment, the size of the cutting punch (e.g., diameter) is about 20% to about 30% of the spacing distance. In one embodiment, the size of the cutting punch (e.g., diameter) is about 30% to about 75% of the spacing distance. In one embodiment, the size of the cutting punch (e.g., diameter) is about 40% to about 75% of the spacing distance. In one embodiment, the size of the cutting punch (e.g., diameter) is about 50% to about 75% of the spacing distance. In one embodiment, the size of the cutting punch (e.g., diameter) is about 60% to about 75% of the spacing distance. This includes ranges or values within any of these ranges (including endpoints).

In one embodiment, the cutting punches are at least 0.5 mm in size (e.g., diameter). In a preferred embodiment, the cutting punches are between about 0.5 mm and about 5 mm in size. In one embodiment, the cutting punches are between about 1 mm and about 5 mm in size. In one embodiment, the cutting punches are between about 2 mm and about 5 mm in size. In one embodiment, the cutting punches are between about 3 mm and about 5 mm in size. In one embodiment, the cutting punches are between about 4 mm and about 5 mm in size. This includes ranges or values within any of these ranges (including endpoints). In one embodiment, the cutting punches are about 0.5 mm in size. In one embodiment, the cutting punches are about 1 mm in size. In an especially preferred embodiment, the cutting punches are about 2 mm in size. In one embodiment, the cutting punches are about 3 mm in size. In one embodiment, the cutting punches are about 4 mm in size. In one embodiment, the cutting punches are about 5 mm in size. In some aspects, the cutting punches are substantially circular.

Figure 6:
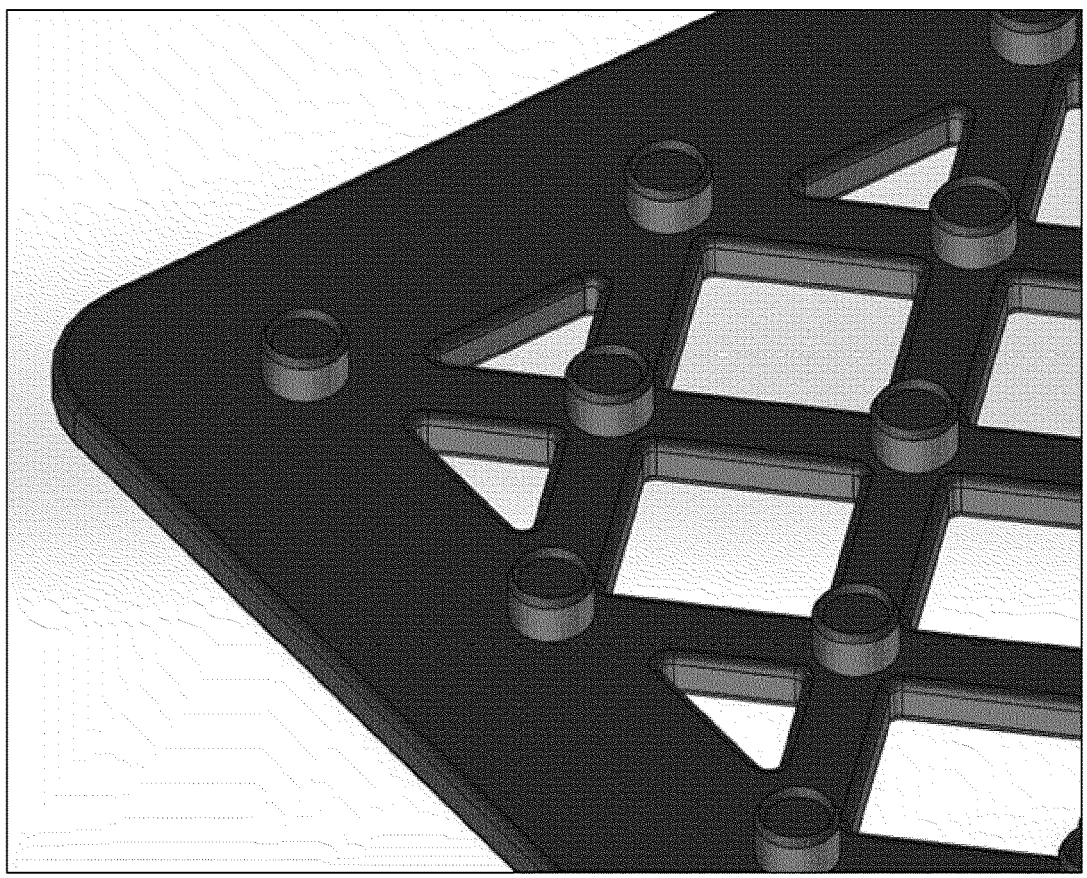
FIG. 6 depicts an exemplary cutting die and cutting punches thereon, according to the present invention.

The cutting punches may be of any shape, as long as exudate can travel through the holes made in the allograft by such cutting punches. In a preferred embodiment, the cutting punches are substantially circular. An exemplary cutting die with circular punches is shown in FIG. 6. In an especially preferred embodiment, the cutting punches are at least about 2 mm diameter.

In a preferred embodiment, the fenestration kit further comprises a bag. In one embodiment, the bag is sized such that the cutting assembly fits therein. The cutting assembly is the combination of the cutting bed with the allograft placed thereon, and the cutting die placed upon the allograft with the cutting punches facing the allograft (i.e., a "sandwich" with the allograft between the cutting bed and the cutting die).

In an especially preferred embodiment, the cutting die, cutting bed, and the bag are sterilizable. In one embodiment, the cutting die, cutting bed, and at least the interior of the bag are sterile. Sterilization may be by any method, including but not limited to gamma irradiation, ultraviolet irradiation, autoclaving, or chemical sterilization. In an especially preferred embodiment, the sterile cutting die and cutting bed are stored and/or transported within the sterilized interior of the bag, as depicted in FIG. 1.

One benefit of the fenestration kit as described herein is that it can be manufactured such that the fenestrations are reproducible between allografts. That is, multiple identical fenestration kits can be manufactured. Uniformity and reproducibility of multiple grafts are important in a commercial setting, and can aid in treatment of wounds as described herein.

Figure 3:
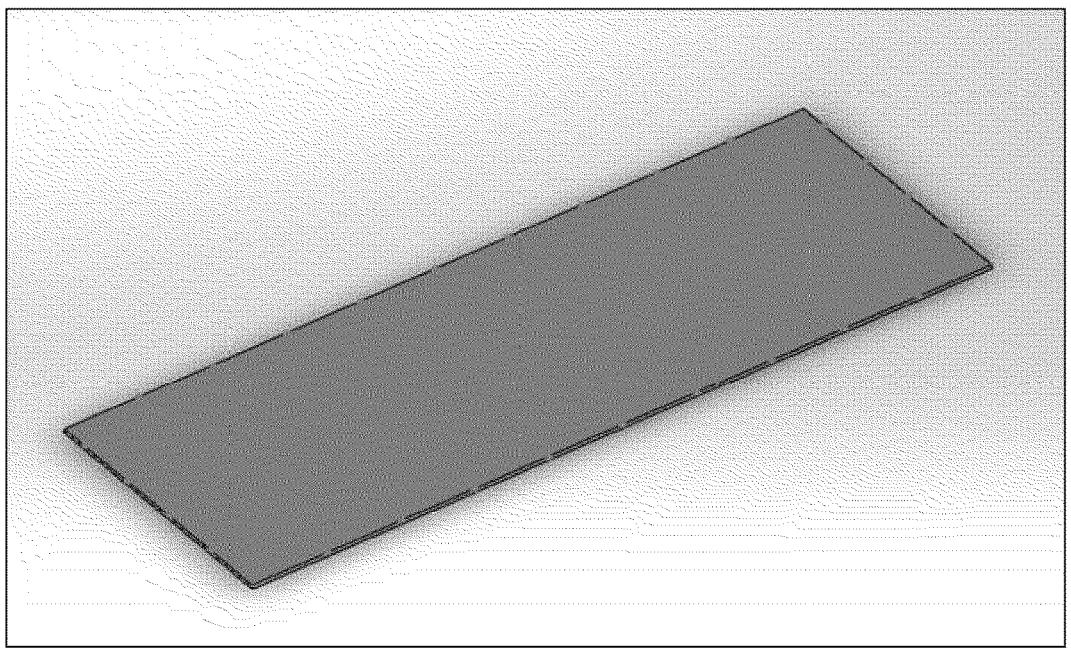
FIG. 3 illustrates a placental tissue allograft placed on top of an exemplary cutting bed according to the present invention.
Figure 4:
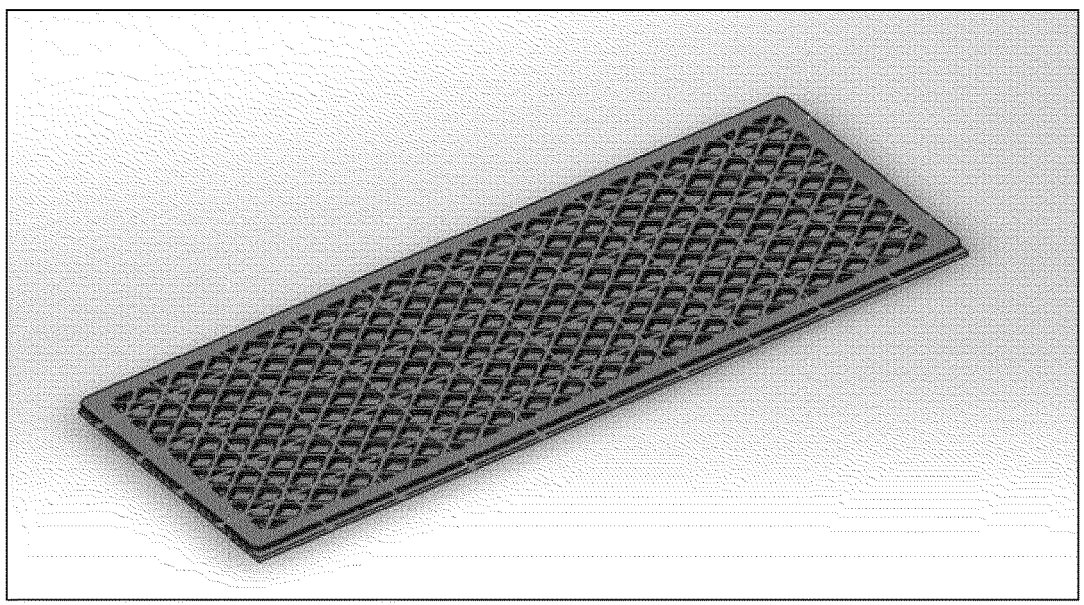
FIG. 4 depicts an exemplary cutting assembly according to the present invention.

All procedures are to be done in an aseptic environment, such as a clean room or biosafety cabinet, using conventional aseptic technique. In order to fenestrate the placental tissue allograft, the allograft is placed on the cutting bed (for example as in FIG. 3). Preferably, the cutting bed is approximately the same size as the allograft, such that the allograft does not overlap the side(s) of the cutting bed and vice-versa. If needed, the allograft may be cut to the appropriate size. The cutting die is placed on top of the allograft, with the cutting punches adjacent to the allograft (FIG. 4). The assembled cutting die/allograft/cutting bed "sandwich" is termed the "assembled fenestration kit."

Figure 5:
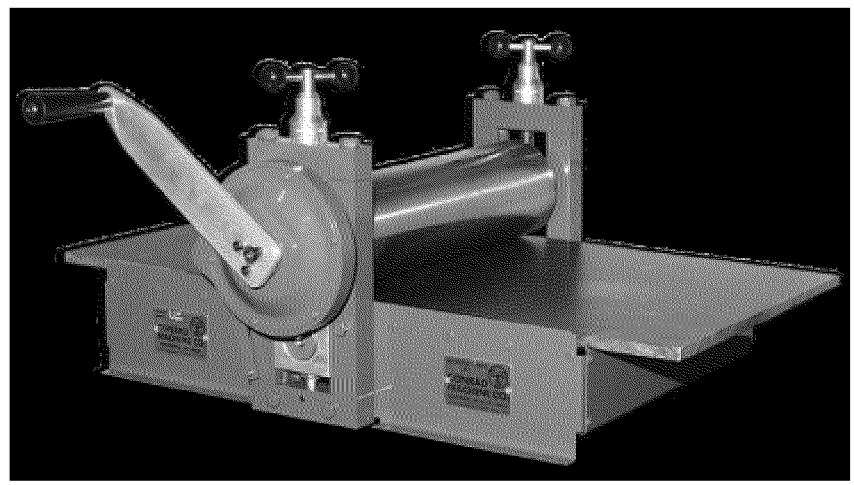
FIG. 5 is an exemplary roller press apparatus through which the cutting assembly may be transported.

In one embodiment, pressure is applied directly to the assembled fenestration kit in order to fenestrate the graft. In a preferred embodiment, the assembled fenestration kit is placed into a bag prior to application of pressure. In an especially preferred environment, the bag is sealed with the assembled fenestration kit inside. Sealing of the bag may be by any method, including adhesive, heat seal, and the like. Pressure is applied to the assembled fenestration kit such that the cutting punches perforate the allograft, thereby fenestrating the allograft. In one embodiment, the pressure is applied manually. In one embodiment, the pressure is applied by a machine, for example a roller press. An exemplary roller press is shown in FIG. 5.

Preferably, pressure is applied uniformly to the allograft within the assembled fenestration kit. Uniform pressure refers to application of approximately the same amount of pressure to the entirety of the assembled fenestration kit, although such pressure need not be applied to the entire kit at the same time. For example, a roll press has a sweeping pressure point at the point of tangency on the fenestration kit (punch/tissue/die). As the kit rolls through the press, the line of pressure will always be at that tangent point and releasing as it gets farther from the tangent point. So, in the instance of a roll press it is uniform across the roller (in a line) as the kit passes through, but not uniform across the entire surface of the die at one time.

A press of a different type (pneumatic, or rack and pinion arbor press) may provide uniform pressure throughout the kit at one time. The force that would be required to achieve the same pressure of the concentrated line of pressure from a roll press would be higher with such presses.

Use of a bag and/or fenestration kit allows considerable flexibility with regard to the fenestration procedure. For example, if the pressure is applied to the assembled fenestration kit inside a sealed bag, then this step need not be performed in the aseptic environment. The process is more efficient and/or faster because multiple allografts (potentially from different donors) can be fenestrated sequentially without need for cleaning and decontaminating the tools (e.g., roller press, fenestration kit, and the like) between each allograft. Further, the risk of contamination of one allograft by placental tissue from a different donor is reduced. Heretofore, the same tools (e.g., punches) were cleaned and reused for multiple allografts. The present invention allows for single-use fenestration kits that eliminate the risk of cross-contamination via these tools.

In a preferred embodiment, the fenestrated allograft is completely free of non-autologous tissue. This is easily achieved by a single use application of the device wherein non-autologous tissue is not introduced into the fenestration device.

In one embodiment, the disposable fenestration kit can be used multiple times prior to disposal. In such embodiments, it is contemplated that the kit is cleaned between subsequent uses as the amount of bioburden carried over from previous allografts is insufficient to warrant replacement when properly cleaned. If necessary, cleaning can include a sterilization step This is also true for fenestration kits that are reusable. In either embodiment, the fenestration kit allows automation of the fenestration process.

In one embodiment, the fenestrations are spaced from about 5 mm to about 20 mm apart as measured from the center of two adjacent fenestrations. In one embodiment, the fenestrations are spaced from about 10 mm to about 20 mm apart as measured from the center of two adjacent fenestrations. In one embodiment, the fenestrations are spaced from about 5 mm to about 10 mm apart as measured from the center of two adjacent fenestrations. This includes ranges or values within any of these ranges (including endpoints). In one embodiment, the fenestrations are spaced about 5 mm, about 6 mm, about 7 mm, about 8 mm, about 9 mm, about 10 mm, about 11 mm, about 12 mm, about 13 mm, about 14 mm, about 15 mm, about 16 mm, about 17 mm, about 18 mm, about 19 mm, or about 20 mm apart as measured from the center of two adjacent fenestrations.

In one embodiment, the fenestrations are spaced from about 1.5 mm to about 10 mm apart as measured from the outer edge of one hole to the closest outer edge of an adjacent hole. In one embodiment, the fenestrations are spaced from about 3 mm to about 10 mm apart as measured from the outer edge of one hole to the closest outer edge of an adjacent hole. In one embodiment, the fenestrations are spaced from about 5 mm to about 10 mm apart as measured from the outer edge of one hole to the closest outer edge of an adjacent hole. In one embodiment, the fenestrations are spaced from about 8 mm to about 10 mm apart as measured from the outer edge of one hole to the closest outer edge of an adjacent hole. This includes ranges or values within any of these ranges (including endpoints). In one embodiment, the fenestrations are spaced about 1.5 mm, about 2 mm, about 3 mm, about 4 mm, about 5 mm, about 6 mm, about 7 mm, about 8 mm, about 9 mm, or about 10 mm apart as measured from the outer edge of one hole to the closest outer edge of an adjacent hole.

In a preferred embodiment, the size of the fenestrations (e.g., diameter) is about 20% to about 75% of the spacing distance between fenestrations. In one embodiment, the size of the fenestrations (e.g., diameter) is about 20% to about 60% of the spacing distance. In one embodiment, the size of the fenestrations (e.g., diameter) is about 20% to about 50% of the spacing distance. In one embodiment, the size of the fenestrations (e.g., diameter) is about 20% to about 40% of the spacing distance. In one embodiment, the size of the fenestrations (e.g., diameter) is about 20% to about 30% of the spacing distance. In one embodiment, the size of the fenestrations (e.g., diameter) is about 30% to about 75% of the spacing distance. In one embodiment, the size of fenestrations (e.g., diameter) is about 40% to about 75% of the spacing distance. In one embodiment, the size of the fenestrations (e.g., diameter) is about 50% to about 75% of the spacing distance. In one embodiment, the size of the fenestrations (e.g., diameter) is about 60% to about 75% of the spacing distance. This includes ranges or values within any of these ranges (including endpoints).

In one embodiment, the fenestrations are at least 0.5 mm in size (e.g., diameter). In a preferred embodiment, the fenestrations are between about 0.5 mm and about 5 mm in size. In one embodiment, the fenestrations are between about 1 mm and about 5 mm in size. In one embodiment, the fenestrations are between about 2 mm and about 5 mm in size. In one embodiment, the fenestrations are between about 3 mm and about 5 mm in size. In one embodiment, the fenestrations are between about 4 mm and about 5 mm in size. This includes ranges or values within any of these ranges (including endpoints). In one embodiment, the fenestrations are about 0.5 mm in size. In one embodiment, the fenestrations are about 1 mm in size. In an especially preferred embodiment, the fenestrations are about 2 mm in size. In one embodiment, the fenestrations are about 3 mm in size. In one embodiment, the fenestrations are about 4 mm in size. In one embodiment, the fenestrations are about 5 mm in size. In some aspects, the fenestrations are substantially circular.

The cutting punches may be of any shape, as long as exudate can travel through the holes in the allograft.

Additional benefits of the fenestration kit as described herein include the reproducibility of the fenestrations made in the allografts, and a decrease in ripping/tearing of the fenestrations as compared with manually punched holes. When holes are manually punched in placental tissue grafts, 5% or more of the holes exhibit tearing or ripping around the edges. Use of the fenestration kit reduces tearing and/or ripping to less than about 2% of the fenestrations. In one embodiment, less than about 1% of the fenestrations exhibit tearing and/or ripping. Reduction of ripping or tearing at the fenestrations is important because dehydrated allografts can be brittle and/or prone to tearing. Tearing/ripping at the fenestrations increases the risk that an allograft will rip during placement. In a preferred embodiment, a ripped or torn fenestration is not adjacent to another ripped or torn fenestration.

In one embodiment, the fenestrations are substantially free of allograft tissue obstruction. As used herein, the term "substantially free" refers to fewer than 20% of the fenestrations have unremoved tissue inside (i.e., blocking or obstructing) the fenestration. In one embodiment, fewer than 10% of the fenestrations have unremoved tissue obstructing the fenestration. In one embodiment, fewer than 5% of the fenestrations have unremoved tissue obstructing the fenestration. In one embodiment, fewer than 4% of the fenestrations have unremoved tissue obstructing the fenestration. In one embodiment, fewer than 3% of the fenestrations have unremoved tissue obstructing the fenestration. In one embodiment, fewer than 2% of the fenestrations have unremoved tissue obstructing the fenestration. In one embodiment, fewer than 1% of the fenestrations have unremoved tissue obstructing the fenestration. Unremoved tissue includes incomplete fenestrations, pieces of allograft that remain partly attached to the allograft within the fenestration, removed pieces of allograft stuck in the fenestrations, and the like.

Cutting & Packaging (Step 160)

Once the placental tissue allograft has been adequately dehydrated, the allograft is then ready to be cut into specific product sizes and appropriately packaged for storage, terminal sterilization, and later surgical use. In one aspect, the bag containing the dehydrated tissue is placed back into the aseptic/controlled environment. The number of grafts to be produced is estimated based on the size and shape of the tissue on the drying fixture(s) or cutting bed(s). An appropriate number of pouches, one for each allograft, is also introduced into the aseptic/controlled environment. The drying fixture(s) or cutting bed(s) are then removed from the bag within the aseptic environment.

Any method can be used to cut the allograft. If the drying fixture has grooves, then the following exemplary procedure can be used for cutting the allograft into product sizes. If the drying fixture is configured in a grid pattern, a #20 or similar straight or rolling blade is used to cut along each groove line in parallel. Next, all lines in the perpendicular direction are cut. Alternatively, if the drying fixture has raised edges or blades, then the following procedure can be used for cutting the allograft into product sizes. A sterile roller is used to roll across the drying fixture. Sufficient pressure must be applied so that the dehydrated allograft is cut along all of the raised blades or edges of the drying fixture. In one embodiment, fenestration is performed after cutting but prior to packaging of the allograft.

After cutting, each fenestrated allograft is placed in a respective "inner" pouch. The inner pouch, which preferably has a clear side and an opaque side, should be oriented clear side facing up. The fenestrated allograft is placed in the "inner" pouch so that the texture in the form of text, logo, name, or similar design (if any) is facing out through the clear side of the inner pouch and is visible outside of the inner pouch. This process is repeated for each separate fenestrated allograft.

Each fenestrated allograft is then given a final inspection to confirm that there are no significant tears or holes (other than the fenestrations), that the product size (as cut) is within approximately 1 millimeter (plus or minus) of the specified length and width size and within approximately 250 microns (plus or minus) thick for that particular graft, that there are no noticeable blemishes or discoloration of the fenestrated allograft, and that the textured logo or wording (if any) is readable and viewable through the "inner" pouch.

To the extent possible, oxygen is removed from the inner pouch before it is sealed. The inner pouch can be sealed in any suitable manner; however, a heat seal has shown to be effective. In one aspect, after packaging, the product is terminally sterilized by radiation, using gamma or electron beam sterilization with a target dose of, for example, 17.5 kGy. Next, each inner pouch is separately packaged in an "outer" pouch for further protection, storage, and shipment.

It should be noted that none of the steps described above involve freezing the allograft to kill unwanted cells, to decontaminate the allograft, or otherwise to preserve the allograft. The dehydrated fenestrated allografts described herein are designed to be stored and shipped at room or ambient temperature without need for refrigeration or freezing.

Product Release (Step 170)

Before the fenestrated allograft is ready for shipment and release to the end user, all documentation related to the manufacture, recovery and donor eligibility are reviewed and deemed acceptable by the quality assurance department and the medical director.

Appropriate labeling and chain of custody is observed throughout all of the above processes, in accordance with accepted industry standards and practice. Appropriate clean room and sterile/aseptic working conditions are maintained and used, to the extent possible, throughout the above processes.

Applications of Fenestrated Allografts

Fenestrated placental tissue allografts as described herein can be used in numerous medical applications involving wound healing in a subject. In one aspect, the allografts described herein are useful in enhancing or improving wound healing. In a preferred embodiment, the allografts are useful in treating a wound by promoting wound healing.

The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. Large wounds, including burns, are especially difficult to treat because they expose a large surface area to the environment (and thus infection risk), and are susceptible to potentially painful and debilitating scars. Physicians dealing with chronic wounds are mainly concerned with closing the wound as quickly as possible to minimize the risk of an infection that could lead to loss of limb or life. Chronic wounds are wounds on patients that have comorbidities that complicate or delay the healing cascade. In one aspect, the fenestrated allografts described herein can function as a tissue regeneration template that delivers essential wound healing factors, extracellular matrix proteins and inflammatory mediators to help reduce inflammation, enhance healing, and reduce scar tissue formation.

The fenestrated allografts described herein also act as a wound dressing. The allograft may be laid on top of a skin wound which is otherwise open to the environment, thereby functioning as a barrier. The fenestrations within the allograft allow exudate and transudate from the wound to pass through the allograft. The allograft is in substantially direct contact with the wound and maintains sufficient surface area such that the majority of the wound is covered. Thus, the allograft can provide bioactive factors, scaffold, etc. as required. "Substantially direct contact" refers to contact with the wound, but may be placed over top of, by way of non-limiting example, exudate, medications, micronized placental tissue, a biocompatible mesh, or any other item or medicament as identified by the clinician to be beneficial for healing the wound.

Without being bound by theory, it is believed that the fenestrated allograft will usually be absorbed by a wound, and, if needed, subsequent allografts can be applied over the wound as the previous allograft is absorbed. In some embodiments, the fenestrated allograft is removed prior to absorption, and may be replaced with a subsequent allograft.

The fenestrated allografts as described herein further have reproducible and preferably uniform/symmetrical fenestrations. If subsequent allografts are to be applied to a wound, the fenestrations of the subsequent allografts can be positioned over a portion of the wound that previously had been covered by the allograft. In this way, all portions of the wound is exposed to the beneficial properties of the allograft, albeit at different times.

In one aspect of the invention, exudate is removed from the wound after the allograft is applied to the wound. In one embodiment, the exudate is removed from the surface of the fenestrated allograft. In one embodiment, the exudate is removed by a negative pressure protocol. In one embodiment, the exudate is removed by the presence of a wound dressing applied over the allograft. In one embodiment, the exudate is removed by compression. Determination of the optimal exudate removal method can be determined by the skilled practitioner, and is dependent on factors such as the type of wound, the amount of exudate, the presence/absence of infection, and the like.

What is claimed is:

1. A method for making a fenestrated placental tissue allograft, said method comprising:
   i) providing a fenestration kit, said kit comprising:
      a) a cutting die comprising a substantially flat die surface having predetermined dimensions and having a first side and a second side, said first side having a plurality of prearranged cutting punches thereon, wherein the cutting die is made of a first material; and
      b) a cutting bed having substantially the same dimensions as the cutting die, wherein the cutting bed is made of a second material;
      wherein the first material is harder than the second material; and
      wherein the cutting punches are sized and spaced so as to produce fenestrations which (a) are spaced from greater than 5 mm to about 20 mm apart as measured from the center of two adjacent fenestrations, and/or (b) are between greater than 2 mm to about 5 mm in size;

ii) placing a placental tissue allograft on the cutting bed;
iii) placing the cutting die on top of the allograft such that the first side of the cutting die is adjacent to said allograft, thereby creating an assembled fenestration kit;
iv) placing the assembled fenestration kit into a sealable bag and sealing the bag; and
v) applying pressure to the assembled fenestration kit such that the cutting punches perforate the allograft; thereby fenestrating the allograft.

2. The method of claim 1, wherein the allograft is dehydrated.

3. The method of claim 1, wherein the placental tissue allograft is dehydrated prior to placing the allograft on the cutting bed.

4. The method of claim 1, wherein the placental tissue allograft comprises a first membrane and a second membrane.

5. The method of claim 4, wherein the first membrane comprises amnion, chorion, or a laminate comprising one or more layers of amnion with one or more layers of chorion.

6. The method of claim 4, wherein the second membrane comprises amnion, chorion, or a laminate comprising one or more layers of amnion with one or more layers of chorion.

7. The method of claim 4, wherein the first membrane comprises modified amnion having a first side which is an exposed basement membrane and a second side which is an exposed fibroblast layer comprising fibroblast cells, and optionally wherein the second membrane comprises chorion and the chorion is adjacent to the second side of the amnion.

8. The method of claim 4, wherein the first membrane comprises modified amnion having a first side which is an epithelial layer and a second side which is an exposed fibroblast layer comprising fibroblast cells, and optionally wherein the second membrane comprises chorion and the chorion is adjacent to the second side of the amnion.

9. The method of claim 4, wherein the first membrane and/or second membrane are cross-linked.

10. The method of claim 1, wherein the first material and/or second material is disposable.

11. The method of claim 1, wherein the first material is selected from the group consisting of polypropylene, styrene, high impact polystyrene, polyvinylchloride, nylon, high density polyethylene, and stainless steel.

12. The method of claim 1, wherein the second material is selected from the group consisting of low density polyethylene, silicone rubber, and isoprene rubber.

13. The method of claim 1, wherein the cutting punches are substantially circular.

14. The method of claim 1, wherein said cutting punches are symmetrically and/or uniformly distributed.

* * * * *